United States Patent [19]

Vaughan

[11] Patent Number: 4,532,347

[45] Date of Patent: Jul. 30, 1985

[54] MEMBRANE SOLVENT EXTRACTION PROCESS

[75] Inventor: Ronald J. Vaughan, Orinda, Calif.

[73] Assignee: Varen Technology, Marshallton, Del.

[21] Appl. No.: 114,379

[22] Filed: Jan. 21, 1980

Related U.S. Application Data

[63] Continuation-in-part of Ser. No. 929,004, Jul. 28, 1978, abandoned, which is a continuation of Ser. No. 479,161, Jun. 13, 1974, abandoned.

[51] Int. Cl.$^3$ .................... C01B 31/20; C07C 51/27; C07C 51/305; C07C 51/31; C07C 55/14; C07C 127/15; C07D 301/14; C07J 1/00

[52] U.S. Cl. .................... 562/528; 210/638; 568/907; 260/397.3; 570/259; 260/397.5; 570/261; 260/410.9 R; 260/417; 423/437; 549/525; 560/24; 560/132; 560/157; 560/204; 560/231; 560/246; 560/265; 562/527; 562/529; 562/530; 562/543; 562/593; 564/57; 568/6; 568/357; 568/360; 568/361; 568/363; 568/403; 568/485; 568/557; 568/833; 568/836; 568/877; 568/880

[58] Field of Search .............. 562/528, 527, 538, 529, 562/530, 543; 210/22 C, 22 R, 637, 638; 560/204, 246, 265, 231, 157, 24, 132; 260/657, 417, 410.9 R, 397.3, 397.5; 568/907, 833, 836, 880, 877, 357, 557, 6, 485, 361, 403, 363; 423/437; 564/57; 570/259, 261; 549/525

[56] References Cited

U.S. PATENT DOCUMENTS

| | | | |
|---|---|---|---|
| 2,923,749 | 2/1960 | Lee et al. | 210/22 C |
| 3,299,157 | 1/1967 | Baddour et al. | 260/674 |
| 3,784,399 | 1/1974 | Grot | 117/62.1 |
| 3,956,112 | 5/1976 | Lee et al. | 210/22 C |

Primary Examiner—Vivian Garner
Attorney, Agent, or Firm—Charles J. Tonkin

[57] ABSTRACT

The instant invention relates to a membrane solvent extraction and reaction system. More particularly it pertains to an improvement in the membrane solvent extraction system wherein a solute is extracted through a polymeric membrane from one solvent liquid phase to an extracting solvent liquid without direct contact between the liquid phases which are separated by the membrane and in which the extracting solvent has no greater solubility and usually substantially less solubility for the solute than the feed solvent. The impovement comprises converting the solute permeating across the membrane to a different chemical compound, whereby a high concentration gradient for the solute across the membrane is maintained to improve the separation of the solute from the feed solvent liquid phase. This improved process is particularly useful for the separation of partially oxygenated hydrocarbons from admixture with hydrocarbons and conversion of the permeating oxygenated hydrocarbons by oxidation in an extracting aqueous solvent containing an oxidizing agent, and in which extracting solvent the oxygenated hydrocarbon solute is less soluble than in the hydrocarbon solvent. This process is especially useful for the separation of the oxidation products of cyclohexane, e.g., cyclohexanol and cyclohexanone, by permeation through a hydrophilic membrane, e.g., fluorocarbon polymers containing pendant sulfonic acid and/or carboxylic acid groups and the salts thereof, into an aqueous solvent comprising an oxidant, e.g., nitric acid. In this embodiment, the oxidation products of cyclohexane may be continuously separated from unoxidized cyclohexane and converted into adipic acid.

10 Claims, No Drawings

MEMBRANE SOLVENT EXTRACTION PROCESS

This patent application is a continuation-in-part of U.S. Ser. No. 929,004, filed July 28, 1978 which in turn is a continuation of U.S. Ser. No. 479,161, filed June 13, 1974, both now abandoned.

FIELD OF THE INVENTION

This invention is concerned with a combined membrane solvent extraction and reaction system whereby an improved separation and removal of solute from admixture with a feed solvent through a separating membrane into an extracting solvent is obtained. More particularly the invention is an improvement in membrane solvent extraction systems wherein a solute is extracted through a separating polymeric membrane from a feed solvent phase to an extracting liquid phase in which the solute has no greater, and preferably less, solubility than in the feed solvent; the improvement comprises converting the solute diffusing or permeating across the membrane to a different chemical compound, whereby a high concentration gradient for the solute across the membrane is maintained to improve (including to increase the rate of) separation of the solute from the feed solvent liquid phase. This process is especially useful for the removal of oxygenated hydrocarbons from mixtures of hydrocarbons and oxygenated hydrocarbons and reaction by the further oxidation of the oxygenated hydrocarbons to organic acids and diacids. In one preferred embodiment of the process of this invention, cyclohexanol and cyclohexanone are continuously removed from cyclohexane, during the liquid phase, air oxidation of cyclohexane by permeation through a membrane comprising a fluorocarbon polymer, said polymer containing pendant sulfonic acid and/or carboxylic acid groups and/or the salts thereof, into an aqueous nitric acid solution, and are further oxidized to adipic acid in said nitric acid solution.

BACKGROUND OF THE PRIOR ART

A membrane solvent extraction process is disclosed in Lee et al U.S. Pat. No. 3,956,112 as an improvement over conventional solvent extraction. Lee et al describes the membrane solvent extraction system as a process comprising the steps of contacting one side of a polymeric substantially non-porous membrane with a feed solvent liquid B containing a solute material A and contacting the other side of the membrane with an extracting solvent liquid C which is substantially immiscible with liquid B, the membrane being swollen by the solvents thereby forming an intermediary zone and allowing diffusion through the swollen membrane of the solute A while preventing direct phase to phase contact between solvents B and C. Diffusivity of A in the membrane between the feed solvent and the extracting solvent is specified in terms of Fick's equation as being in the range of about $1 \times 10^{-9}$ to about $1 \times 10^{-4}$ cm$^2$/sec. In this system the removal of solute A from the feed solvent liquid into the extracting solvent liquid C depends not only on diffusivity but on the relative solubilities of the solute A in the solvents B and C, i.e., to obtain substantial removal of solute A from feed solvent B the solubility of solute A in the extracting solvent C must be substantially greater than in the feed solvent B or large volumes of extracting solvent C must be used; i.e., the distribution of solute A between the feed solvent and the extracting solvent will not go beyond the partition coefficient of solute A.

As background with respect to a preferred embodiment of this invention, the conversion of cyclohexane into adipic acid by processes comprising liquid phase air oxidation of cyclohexane to a mixture comprising cyclohexanol, cyclohexanone and unreacted cyclohexane, followed by separation of the unreacted cyclohexane, and nitric acid oxidation of the cyclohexanol and cyclohexanone mixture to give adipic acid is disclosed in U.S. Pat. Nos. 2,439,513 and 2,557,282. Such processes have provided a commercially valuable route to adipic acid, which is an ingredient for the production of nylon.

Polymerization of adipic acid with hexamethylenediamine yields polyhexamethyleneadipamide, i.e. nylon, which is useful in various textile and plastic applications, and is manufactured on a scale of many millions of pounds per year. Therefore, processes for the production of adipic acid which are more economical are commercially valuable. The processes taught in the above patents provide very low yields of adipic acid from cyclohexane, thus resulting in excessive capital investment, excessive usage of energy during processing and excessive consumption of raw materials, particularly cyclohexane. In particular, excessive energy is required for separating the cyclohexane from the cyclohexanol and cyclohexanone by the separation processes, e.g., steam distillation, taught therein. It is clear from a careful reading of the above patents that membrane separation processes were not contemplated by the patentees.

In the processes disclosed in the above patents, the cyclohexane oxidation step is normally carried out to low levels of cyclohexane conversion, e.g., about 6% to 8%, to minimize degradation of cyclohexanol and cyclohexanone to products unsuitable for the following nitric acid oxidation step. One particular embodiment of the instant invention avoids this problem by continuously removing the cyclohexane oxidation products, e.g., cyclohexanol and cyclohexanone, as they are formed.

Processes for continuous separation of reaction products of organic chemical reactions are known in the art. See, for example, U.S. Pat. No. 2,956,071, which teaches a process for continuously removing water, which is formed as a reaction product from organic chemical reactants, e.g., as in esterification reactions. This process utilizes hydrophilic membranes to continuously remove water and drive the reaction to completion. This process differs from the process of the instant invention in substantial ways. For example, the patented process contemplates the use of cation exchange materials as catalysts for esterification rather than the conventional strong acid esterification catalysts, e.g. sulfuric acid, which would attack the membrane. In the process of the instant invention, this problem may be avoided by careful selection of the membrane material. Thus in one preferred embodiment, a fluorosulfonic acid polymer membrane is utilized in a strong acid environment, thus avoiding the problems relating to use of a cation exchange material as a catalyst.

The instant process also differs in other substantial ways. For example, unlike the prior art process, the instant process is driven by continuous reaction as well as diffusion, i.e. the process proceeds by reacting a compound which has crossed the membrane and thus maintaining a high concentration gradient.

SUMMARY OF THE INVENTION

The instant invention relates to a combined membrane solvent extraction and reaction system for separating and removing a solute from admixture with a feed solvent through a polymeric membrane into an extracting solvent and converting the solute to another chemical compound as it crosses the membrane into the extracting solvent. This invention is an improvement over membrane solvent extraction processes such as described in Lee et al U.S. Pat. No. 3,956,112, the disclosure of which is incorporated herein by reference. In accordance with this invention, the separation and removal of a solute A from a feed solvent liquid B through a membrane into an extracting solvent liquid C is not directed to pairs of solvents where the solubility of the solute A in the extracting solvent C is substantially greater than in feed solvent B as in the Lee et al patent but is directed to solvents where the solubility of solute A in the extracting solvent C is no greater, and preferably substantially less, than its solubility in the feed solvent. A preferred embodiment of the instant invention, as will be illustrated hereinbelow, is directed to the use of an extracting solvent C which has less solubility for solute A than the feed solvent B (i.e., the solute in such embodiment may be at least five times more soluble in the feed solvent than in the extracting solvent); this illustrates the invention with a solute-solvent pair system in which separation of the solute is normally more difficult.

More particularly, the instant invention relates to a method for separating oxygenated hydrocarbons from fluid mixtures containing said oxygenated hydrocarbons which comprises introducing said mixture into the feed zone of a permeation apparatus, said permeation apparatus comprising a feed zone and a permeate zone separated by a polymer membrane which is permeable to said oxygenated hydrocarbons, providing a solvent for said oxygenated hydrocarbons in said permeate zone, and converting, such as by oxidizing, said oxygenated hydrocarbons permeating through said membrane to maintain a high concentration gradient of said oxygenated hydrocarbons across said membrane.

In one embodiment of the instant invention, a feed stream comprising one or more $C_4$-$C_{12}$ hydrocarbons, e.g., alkanes, cycloalkanes, aromatics, alkyl substituted aromatics, etc., preferably $C_4$-$C_6$ cycloalkanes is subjected to liquid pahse oxidation in the feed zone of said permeation apparatus and the reaction products are continuously removed by permeation through membrane into a solvent for said reaction products which is provided in said permeate zone. A high concentration gradient across the membrane is maintained by further reaction of the oxygen-containing reaction products in said permeate zone, for example, as by further oxidation.

In the most preferred embodiment of the instant invention, cyclohexanol and cyclohexanone are separated from cyclohexane by permeation through a membrane into an aqueous solvent phase wherein an oxidizing agent, e.g. nitric acid, is contained. In this embodiment, cyclohexanone and cyclohexanol are converted by the aqueous nitric acid into adipic acid. Thus, the instant invention contemplates a process wherein cyclohexane-containing feed streams are oxidized by contact with an oxygen-containing gas at a temperature of from 40° C. to 200° C. and a pressure of from 30 to 500 psi in the presence of an oxidation catalyst and thereby converted into a mixture comprising cyclohexanol, cyclohexane, as well as various other oxidation products of cyclohexane, which are continuously removed after their formation by permeation across a membrane into an aqueous nitric acid phase which is maintained at a temperature of from 40 to 200° C. and a pressure of from 30 to 500 psi. With some membranes, particularly the preferred perfluorocarbon polymer with pendant sulfonic acid groups, and with water present, the temperature can be as high as 250° C. and the pressure may be as high as 800 psi. The nitric acid phase may further comprise a catalyst for the conversion of cyclohexanol and cyclohexanone into adipic acid, e.g. cupric nitrate.

The membrane used in the process of the instant invention may be employed in the form of films, sheets, tubes and hollow fibers. The membrane functionally must permit the passage of the oxygenated reaction products and be substantially or relatively impervious to the passage therethrough of the unreacted hydrocarbons. The membrane material must be chemically stable when contacted with various components of the reaction environments, for example, in the preferred embodiment of the instant invention, wherein cyclohexane is continuously oxidized in the feed zone of the permeation apparatus, and the oxygenated products continuously removed by permeation into an aqueous nitric acid media, the membrane must be resistant to hydrocarbons as well as strong oxidizing acids at temperatures of from 50 to 200° C.

In accordance with the invention, several kinds of membranes may be used. The selection of the optimum membrane may depend on the particular environment of its use, e.g., the stability of the two solvents, the resistance to reaction with the reactants in the conversion step and to the reaction products thereof and its ability to allow the solute to diffuse through the membrane. The diffusion of a solute through a membrane can readily be determined, as will be apparent to one skilled in the art, by using a dialysis or cavity cell having a feed solvent in admixture with the solute on one side of the membrane and the extracting solvent on the other side and monitoring the appearance of the solute in the extracting solvent which may be dependent on parameters of membrane thickness, ionic form and temperature. In the aforementioned Lee et al U.S. Pat. No. 3,956,112, diffusivity is measured in terms expressed by Fick's equation and therein diffusivity is required to be at least $1 \times 10^{-9}$ cm$^2$/sec. While the present invention applies beneficially where there is any appreciable diffusivity for the solute, the membranes having the higher diffusion characteristics for the solute while minimizing diffusion of the solvents are preferred. (Throughout, the terms "diffusion", "permeating" and "permeability" are used interchangeably in the limited sense to indicate a process of mass transfer and not direct passage of liquids through direct channels through the non-porous membrane.)

Generally the various membrane materials described in Lee et al U.S. Pat. No. 3,956,112 can be used in accordance with the improved instant invention. Preferably the separation of oxygenated hydrocarbons is accomplished with the hydrophilic polymer membranes. More particularly, the invention is preferably carried out using fluorocarbons, silicones, polyamides, polyimides, polyesters and hydrocarbon polymers which have been modified by copolymerization or grafting to incorporate hydrophilic groups.

The preferred membrane materials are the fluorocarbon polymers which may contain pendant groups such as sulfonic acid and/or carboxylic acid groups and salts of the acids as well, and may be derived from fluorocarbon polymers having mixed chlorine and fluorine substituents, wherein the number of chlorine atoms is not more than about 20% of the total chlorine and fluorine atoms present in said polymer. A particularly applicable material for making the membranes useful in the present invention comprises a solid perfluorocarbon polymer having either pendant sulfonic acid or sulfonate groups or both sulfonic acid and sulfonate groups. Said perfluorocarbon polymer has the pendant groups attached either directly to the main polymer chain or to the perfluorocarbon side chains attached to the main polymer chain. Either or both the main polymer chain and any side chain may contain oxygen atom linkages such as ether linkages as in Nafion* perfluorosulphonic acid membranes obtained from E. I. duPont de Nemours and Co. (see description given in INNOVATION, Vol. 4, No. 3 (1973) pp. 10-13). The perfluorocarbon polymers particularly useful in the present invention may be prepared as disclosed in U.S. Pat. Nos. 3,041,317; 3,282,875 and 3,624,053 hereby incorporated by reference. The preferred perfluorocarbon polymers are prepared by copolymerizing perfluorovinyl ether having the formula $FSO_2CF_2OCF(CF_3)CF_2OCF=CF_2$ and tetrafluoroethylene followed by conversion of the $-SO_2F$ group to either a sulfonic acid group or sulfonate group or both. The equivalent weight of the preferred copolymers preferably range from 850 to 2500 where the equivalent weight is defined as the average molecular weight per sulfonyl group.

The preferred thickness of the membrane ranges from 0.0001 to 0.250 inches, preferably from 0.001 to 0.025 inches.

The process of the instant invention is carried out at as high a temperature as is suitable for the membrane material in contact with the feedstream and the solvent for the reactants. Higher temperature increases the diffusion rate thus yielding a more economical process. The membrane is provided in as low a thickness as possible consistent with physical strength under the operating conditions selected in order to increase permeation rate across it.

The feed and the extracting solvent are brought into their respective zones of the permeation apparatus on either a continuous or intermittent basis. In general, both the solvent and the feed will be continuously flowed through the apparatus in contact with the membrane. The extracting solvent and the feedstream may be flowed across the membrane in either a concurrent or countercurrent relationship. The temperature maintained in the permeation apparatus is in the range of from 40 to 250° C., preferably from 50 to 180° C. Pressure may range from 0 to 800, preferably from 0 to 250 psi. Preferably, temperature and pressure are adjusted so that both the feedstream and the extracting solvent are maintained in a liquid phase.

In the preferred process for preparing alipic acid from cyclohexane, a mixture comprising cyclohexane and its oxidized reaction products may be either formed in the feed zone of the permeation apparatus, or alternatively, the oxidized reaction product may be formed prior to bringing it into the permeation apparatus. The membrane in this instance may be prepared from a fluorosulfonic acid polymer, e.g. Nafion.

The membrane may be supported on filters and/or fabrics, perferably filters or fabrics of Teflon TFE resins; and/or porous metal or ceramic supports wherein the membrane is placed on the surface of said support, e.g. wire screen of stainless steel (316 or 304); titanium, etc. The support must be sufficiently porous to permit permeation and solvent removal.

One mode of carrying out the process of the instant invention, utilizes the above membrane material in the form of hollow fibers. See, for example, the hollow fiber reactor described in U.S. Pat. Nos. 3,228,876 and 3,956,112 hereby incorporated by reference which may be used in carrying out the process of the instant invention, provided said hollow fibers are within the above description of the membrane materials.

While the preferred membrane materials are those that are swollen by the respective solvents, generally it is only required that the polymeric membrane have sufficient solubility for the solute so that the solute diffuses through the membrane.

The extracting solvent and the feed solvent liquid containing the solute are preferably immiscible, do not diffuse or permeate appreciably through the membrane and do not react with the conversion reactant or solute. The feed solvent liquid, as indicated above, is preferably hydrocarbon but also may be other liquid solvents for the solute such as partially oxygenated hydrocarbons, e.g., alcohols, ketones, esters, acids, etc. which are different from the solute, i.e., as compared to the solute, the solvent has substantially less, and preferably essentially no, chemical reactivity with the reactant and/or substantially less, and preferably essentially no, permeability through the membrane. The extracting solvent liquid is any liquid which has at least slight solubility for the solute. In a preferred embodiment where the solute is a partially oxygenated hydrocarbon such as an alcohol or ketone or mixtures thereof, in a hydrocarbon feed solvent liquid the extracting solvent can be aqueous in which most partially oxygenated hydrocarbons are less soluble than in hydrocarbon. The solute can be a variety of compounds and in a preferred embodiment is a partially oxygenated hydrocarbon, especially alcohols and ketones. The solute will generally be present in a minor amount in the feed solvent. The invention also has particular application to feed solvents containing very small or trace amounts of solute, where it is desired to use the present membrane extraction and conversion process to strip such small amounts from the feed solvent; for example, small amounts such as 0.1% methanol can be removed from benzene into water by converting the methanol in the aqueous phase to carbon dioxide by oxidation with nitric acid or other suitable oxidant. Thus, the invention is applicable where the amount of solute is enough to make removal or recovery desirable.

The reactants used for converting the permeating solute to another substance are those which are not reactive with the solvents or the selected membrane and will not diffuse to an appreciable extent through the membrane. As will be recognized by one skilled in the art, the reactant chosen will depend upon the nature of the solute and the nature of the reaction products desired. The reactant will be capable of reacting with the permeating solute to convert it to a different chemical compound (i.e., a chemically distinct substance); the reaction should involve a total free energy change ($\Delta G$) of at least 1 kcal/mol of solute; a $\Delta G$ of 7-10 kilo calories will be quite satisfactory. The reaction will be exothermic and the reaction products will be relatively stable. The preferred reactions give substantially different compounds such as the change from alcohol to ketone or acid and preferably are not simple neutralizations of acids with bases. Thus the conversion of the solute to a different chemical compound is by reaction with a reactant which is reactive with the solute but is essentially non-reactive with the membrane and the solvents. Thereby a high concentration gradient across the membrane is maintained to improve (by increasing the rate and/or amount) the separation of the solute from admixture with the feed solvent. A preferred class of reactants are oxidants capable of converting the permeating solute such as partially oxygenated hydrocarbons, e.g., alcohols and ketones, to a different substance, such as oxygenated hydrocarbons at a higher oxygenated state, such as acids. Suitable oxidants are various oxidizing agents with or without oxidation catalysts, and include aqueous nitric acid, chromic acid, peracids such as peracetic acid, peroxy disulfate, halo oxides such as chlorine dioxide, permanganate, perchlorate, hypochlorite, and periodate. Oxidation catalysts such as cupric nitrate and vanadium nitrate can be added to aqueous nitric acid. Other reactants capable of converting the permeating solute to a different substance such as to a more polar compound include esterifying agents (usually with alcohol as the solute) such as acid chlorides, acid anhydrides, and acetyl imidazole; isocyanates (with alcohols), and reducing agents such as the metal hydrides such as lithium aluminum hydride, and boron hydrides. With ethers as the solute, Lewis acid complexes such as $AlCl_3.BF_3$ or halogen acids can be used to convert the ethers to oxonium salts or cleavage products such as alcohols and alkyl halides.

The reaction conditions are preferably as indicated hereinabove but generally are adjusted to promote the selective reaction and conversion of the permeating solute while maintaining the solvents in the liquid phase, i.e., above their freezing points and below their boiling points, and taking into account the nature of the membrane employed (i.e., below the point of appreciable softening and disintegration of the membrane). There will be advantages with some materials where the resulting reaction product in each case: is more soluble in the extracting solvent than the solute, does not diffuse or permeate back to the feed solvent, does diffuse back to the feed solvent (in a secondary extraction mechanism) or is insoluble in the extracting solvent (allowing ready removal by filtration).

The reaction products will depend, as will be apparent to one skilled in the art, on the nature of the solute and the reactant. Thus, with alcohols as the solute the reaction products in the case of oxidative conversion can be ketones and acids (methanol may go to carbon dioxide); in the case of esterification will be esters and in the case of reaction with isocyanate will be carbamates or urethanes. With ketones, oxidation will yield acids or diacids and reduction will yield alcohols. With ethers, reaction with halogen acids will yield oxonium salts and reaction with cleavage agents such as Lewis acid complexes will yield alcohols and alkyl halides. With esters, saponification will yield alcohols and acid salts.

The following uses a preferred embodiment of separating cyclohexanol and cyclohexanone from cyclohexane, and is illustrative of a preferred procedure for carrying out the invention: An aqueous nitric acid mixture, i.e. from 10 to 70 wt. % nitric acid, e.g., 41 % nitric acid, is introduced into the permeate zone. The cyclohexane mixture and the nitric acid mixture are preferably flowed in a countercurrent manner. The feed and the solvent may be brought into the permeation apparatus through conduits, which are connected to separate fluid reservoirs. The feed mixture may comprise from 0.1 to 15, preferably 1 to 5 wt. % each of cyclohexanol and cyclohexanone, the remainder being cyclohexane, or cyclohexane may be oxidized in the feed zone to cyclohexanol and cyclohexanone which are continuously removed. The temperature is maintained at from 40 to 105° C. The cyclohexanone and cyclohexanol permeate across the fluorosulfonic acid polymer membrane into the aqueous nitric acid solution which may additionally comprise an oxidation catalyst, e.g., cupric nitrate, e.g. from about 0.01 to 0.5 wt. % copper. The cyclohexanone and cyclohexanol are continuously removed by conversion into adipic acid in the permeate zone. The adipic acid may be recovered from the aqueous nitric acid solution by various methods known in the art. For example, the aqueous nitric acid solution may be cooled in the permeation zone down to about 5° C. or less, and crystallized adipic acid filtered off. The aqueous nitric acid filtrate could then be concentrated for reuse.

Variants of the above illustrative procedure will be apparent to those skilled in the art. Thus, the extraction-reaction process can be subdivided into multiple zones; for example, the feed of solvent and solute may be flowed through a central tube of the polymeric membrane with an annular space surrounding the tube containing a flowing extracting solvent (without any reactant) which is in contact with another larger tubular membrane having contained in contact with its outer surface a flowing extracting solvent containing a reactant such as an oxidant. Such a multiple zone system with an intermediate extraction loop allows more flexibility such more optimum temperature control as well as other advantages.

The following are preferred embodiments of the instant invention. There is no intent to be limited to the subject matter disclosed herein.

The reactors used in the experiments described below utilized Nafion* membranes. One was a circular cavity dialysis cell comprising two mating halves (with the Nafion* membrane between) sealed by the mating surfaces of the cells and by a Viton* O-ring on the circumference. To initiate a reaction, a glass bead of 5 mm diameter was placed in each cell half and the mating halves clamped onto a freshly prepared membrane using an external clamping device. The assembled cell was loaded (through the syringe ports) in one half with the feed mixture and equilibrated in a shaking water bath maintained at the desired temperature, "Start of reaction" was noted upon introduction of the aqueous phase into the other half of the cell. The other apparatus was a flow reactor in an "annular tube" design constructed of an inner Nafion* tube (nominal 0.024" I.D.×0.036" O.D.), and an outer tube of (1/16" I.D.×⅛" O.D.×38 ft.) Teflon* with end fittings in a "heat-exchange" configuration. The reactants could be introduced and withdrawn from the inner Nafion* tube (inner tube) or from the annular shell between the Nafion* tube and the inner wall of the Teflon* tubing (outer tube). The volume of the inner tube was approximately 4 ml, the "outer tube" approximately 14 ml. The resulting tubular reactor was coiled around a cylinder of stainless steel screening and immersed in a stirred resin kettle filled with distilled water. Temperature was maintained by a thermistor temperature controller connected to a heating mantle on the kettle.

For the dialysis cell experiments, the Nafion* membrane was routinely prepared by boiling for 0.5 hr. in 10% nitric acid, then boiling briefly in distilled water. For the flow reactor, the membrane tubing was initially prepared by flushing both "tubes" with 10% nitric acid at 60°. Thereafter the reactor was flushed with feed (e.g. cyclohexane) and water (in the appropriate "tubes") at the conclusion of each reaction. For the reactions utilizing cyclohexane, flow in both "tubes" was provided by a calibrated syringe pump. For the reactions with cyclododecane, hydrocarbon flow was provided by pressuring a heated metal cylinder containing the molten ketone-hydrocarbon mixture to 5–10 psi with dry nitrogen, and allowing the mixture to exit through a dip tube and metering valve.

Product analysis was performed on a Varian-Aerograph 1200 Series gas chromatograph equipped with a temperature programmer, flame ionization detector and a Disc* integrator on the recorder. Samples taken from the feed phase were routinely diluted with an aliquot of cyclohexane containing a known concentration of 2-methoxy ethanol to provide an internal standard. Samples from the water phase in diffusion experiments were similarly diluted with a known concentration of 2-methoxyethanol in water and chromatographed directly. Diacid products were converted to the dimethyl esters for gas chromatographic analysis: Aliquots from the hydrocarbon or nitric acid phase were diluted with a known concentration of pimelic acid, then evaporated to dryness in vacuo (1–3 mm, less than 50°). The residue was taken up in $BF_3$-methanol (0.5 ml, 14% w/vol) and refluxed 5 min. to complete the esterification. The tubes were cooled, chloroform (0.5 ml) and water (1.5 ml) were added, then the tubes were stoppered, shaken, and the layers allowed to separate. The chloroform layer was analyzed directly on the gas chromatograph to determine the amounts of adipic and other acids.

Columns used for analysis were a $5' \times \frac{1}{8}''$ (O.D.) column of 3% STAP on 100/120 Varoport #30 and a $10' \times \frac{1}{8}''$ column of 10% (w/w) Carbowax 20M on 100/120 mesh HMDS-Chromosorb W.

Values obtained from the Disc* integrator were referenced to the internal indicator and corrected for the relative response of each compound on the flame ionization detector to obtain actual concentrations of the original sample. In some parts of the work on cyclododecanone oxidation, the use of an internal indicator on the hydrocarbon side became excessively difficult; in these cases comparison was made by replicate injection of identical samples (using a 1 ml syringe) of a known concentration of the compound being analyzed.

Thicknesses of sheet membranes are those before swelling in solvent.

EXAMPLE 1

Selective extraction of cyclohexanol and cyclohexanone from a hydrocarbon phase was explored by placing a feed solution of 5% by weight (each) of cyclohexanone and cyclohexanol in cyclohexane on one side of the Nafion* membrane and water on the other side in the above-described dialysis cell. The membrane was in the acid form and had a thickness of 0.005". The appearance of ketone and alcohol in the water phase was monitored as a function of time. The results showed a first order approach to equilibrium for a system in which ketone and alcohol can diffuse in both directions. No diffusion of cyclohexane into the water phase could be detected. The expected equilibrium concentration of cyclohexane would not be high due to its low solubility in the aqueous phase (0.017% at 56° C.). The effect of the ionic form of the membrane and temperature were also explored: in comparing the above membrane with its magnesium salt form, it was noted that the diffusion rate was not appreciably altered. The diffusion rate was decreased by using a membrane having a thickness of 0.013" and increased by increasing the temperature of the extraction from 37° C. to 50° C.

With nitric acid instead of water opposite the ketone-alcohol mixture, adipic acid was produced. The rate of formation of adipic acid is comparable to the rate of ketone and alcohol diffusion, suggesting that under these conditions the rate of reaction is probably controlled by the rate of substrate diffusion.

TABLE I

Dialysis Cell at 60° C.
of 2.0% wt./vol. each
of cyclohexanone and cyclohexanol
in cyclohexane in feed zone
41% aqueous $HNO_3$
in permeate zone
Membrane = 0.005" Nafion
Equivalent Weight = 1200

| Time (minutes) | % Adipic Acid (wt./vol.) |
|---|---|
| 0 | 0 |
| 10 | 0.35 |
| 15 | 0.50 |
| 20 | 0.63 |
| 30 | 0.84 |
| 40 | 1.06 |
| 53 | 1.28 |
| 60 | 1.40 |
| 75 | 1.43 |
| 90 | 1.45 |
| 106 | 1.67 |
| 120 | 1.64 |
| 150 | 1.71 |
| 180 | 1.76 |
| 240 | 1.76 |

At higher concentrations of nitric acid and/or with a copper catalyst, a second membrane-controlled reaction becomes apparent, as some adipic acid forms on the hydrocarbon side of the membrane from the diffusion of nitric acid (or possibly oxides of nitrogen) to the hydrocarbon-membrane interface. To minimize the formation of adipic acid in the feed, $HNO_3$ concentrations are preferably maintained below 50%, more preferably 45% by weight. These preferred concentrations relate to use of a fluorosulfonic acid membrane having an equivalent weight of about 1160. With higher equivalent weights, a higher concentration of $HNO_3$ may be used.

EXAMPLE 2

A flow reactor was constructed using a Nafion* tube inside a larger Teflon* tube: the surface/volume ratio for this reactor is roughly 40 times that for the dialysis cell. Countercurrent flow of the feed vs. water at increasing flow rates showed that equilibration of ketone and alcohol across the membrane at 60° was complete at all water flow rates slower than 2 ml/min., which corresponds to an average residence time for the water phase of 7 min. Concentrations of cyclohexanone and cyclohexanol in the water phase were about 0.5% and 0.75% respectively. Again, no diffusion of cyclohexane was observed.

With nitric acid instead of water opposite the feed, oxidation of ketone and alcohol to a mixture of diacids (principally adipic acid) occurred, as in the dialysis cell reactor. The qualitative characteristics of the reaction were similar to the dialysis cell reaction; however, all rates were increased due to the higher surface/volume ratio. With 41% nitric acid vs. 2.5% w/v each cyclohexanone and cyclohexanol in cyclohexane, all the adipic acid formed was recovered on the aqueous nitric acid side of the membrane (Table II Run a). Under these conditions (low nitric acid concentration, no catalyst, low reaction temperature) the yield of adipic acid product is only 28%, and a substantial portion of the diacids are glutaric and succinic acids. The low recovery is probably due to unreacted ketone and alcohol, although very little residual ketone or alcohol could be detected in the hydrocarbon effluent.

Yield of adipic acid was calculated on the basis of total depletion of the cyclohexane phase and the ratio of flow rates of the nitric acid and cyclohexane phases, e.g. 1% (w/v) each of ketone and alcohol should yield 2.95% (w/v) adipic acid in the nitric acid phase at equal flow rates.

Reaction variables were briefly explored to further optimize the conversion of ketone and alcohol to adipic acid (Table II). Increased temperature increased the conversion to adipic acid; impurities were roughly at the same level, regardless of temperature (Table II Run B). Increased feed flow rate led to a reduction in adipic acid yield (Table II Run C). This parallels the drop in diffusion of ketone and alcohol observed above; however, the yield decreases somewhat more than would be expected from decreased diffusion alone, leading to the possibility that the reaction mixture has too little time to react completely at the higher flow rate. Lowering the concentration of nitric acid to 15% drastically reduced the yield of adipic acid.

The concentration of ketone and alcohol in the cyclohexane phase had no great effect on the conversion to adipic acid up to a concentration of 10% (w/v) each (Table II Run E), at this concentration the depletion of the nitric acid becomes significant, shutting off complete reaction.

The ratio of nitric acid flow to feed flow was varied over a four-fold range with little effect on yield of adipic acid or level of impurities (Table II Run F).

Addition of copper and/or vanadium catalyst (e.g. in the range of from 0.01 to 0.05%, and $Cu^{+2}$ in the range of from 0.01 to 0.5%, preferably about 0.1% by weight $Cu^{+2}$;) to the nitric acid greatly increased the yield of adipic acid and decreased the level of impurities (Table II Run G); however, the catalyst also increased the rate of formation of adipic acid on the hydrocarbon side of the membrane, eventually blocking the flow of reactant.

A second series of reactions was undertaken to further optimize conditions for adipic acid production; the results are reported in Table III: Extraction of ketone and alcohol is virtually complete. At this temperature (55°), a nitric acid concentration of about 45% was found to be optimal. For demonstration purposes a low (0.05% w/v) copper concentration was used, although slightly purer adipic acid results from a higher catalyst concentration. Vanadium was somewhat less effective than copper in directing the reaction. Concentrations of ketone and alcohol were low (2.5% w/v each) with a feed flow rate twice that of the nitric acid phase. Under these conditions, the total yield of adipic acid was about 55–60%.

TABLE II

| Concn. (each by wt.) %/vol. of cyclohexanol and cyclohexanone | | HNO$_3$ (Concn % wt/vol) | T (°C.) | Flow Rate Feed (ml/min) | Flow Rate HNO$_3$ (ml/min) | Concn. adipic acid (wt. %) | glutaric/ adipic × 100 | succinic/ adipic × 100 | % yield adipic acid |
|---|---|---|---|---|---|---|---|---|---|
| A | 2.5 | 41% | 55 | 1(concurrent) | 1 | 2.03 | 67 | 21 | 28 |
|   | 2.5 | 41% | 55 | 1 (countcurr.) | 1 | 2.03 | 79 | 25 | 28 |
| B | 2.5 | 41% | 45 | 1 | 1 | 0.78 | 48 | trace | 10 |
|   | 2.5 | 41% | 65 | 1 | 1 | 2.37 | 70 | 26 | 30 |
|   | 2.5 | 41% | 75 | 1 | 1 | 2.54 | 57 | 23 | 34 |
| C | 2.5 | 41% | 55 | 0.51 | 0.51 | 2.0 | 76 | 26 | 27 |
|   | 2.5 | 41% | 55 | 1.0 | 1.0 | 1.73 | 83 | 34 | 24 |
|   | 2.5 | 41% | 55 | 1.96 | 1.96 | 1.12 | 74 | 25 | 15 |
|   | 2.5 | 41% | 55 | 3.84 | 3.84 | 0.78 | 78 | 37 | 11 |
| D | 2.5 | 41% | 55 | 1 | 1 | 0.61 | 26 | trace | 9 |
| E | 1.25 | 41% | 55 | 1 | 1 | 0.94 | 79 | 27 | 25 |
|   | 2.5 | 41% | 55 | 1 | 1 | 2.03 | 67 | 21 | 28 |
|   | 5 | 41% | 55 | 1 | 1 | 3.5 | 64 | 19 | 23 |
|   | 10 | 41% | 55 | 1 | 1 | 4.3 | 67 | 13 | 15 |
| F | 2.5 | 41% | 55 | 1.06 | 1.96 | 0.85 | 59 | 16 | 21 |
|   | 2.5 | .41% | 55 | 1.06 | 1.06 | 1.69 | 71 | 21 | 23 |
|   | 2.5 | 41% | 55 | 1.02 | 0.51 | 3.0 | 75 | 21 | 20 |
| G | 2.5 | 41% 0.2% Cu 0.05% NH$_4$VO$_3$ | 55 | 1 | 1 | 4.2 | 13 | 4 | 57 |

TABLE III

| Concn. (each by wt. %) per unit vol.) cyclohexanol and cyclohexanone | Concn. HNO$_3$ (% w/w) | Catalyst (% w/v) | Flow Rate HNO$_3$ (ml/min) | Flow Rate HC Feed (ml/min) | T | Concurrent or Countercurrent Flow | Adipic Acid (% w/v) | Glutaric/ Adipic (× 100) | Succinic/ Adipic (× 100) | Adipic Acid Yield (%) | Cyclohexanone Residual (% w/v) | Cyclohexanol Residual (% w/v) |
|---|---|---|---|---|---|---|---|---|---|---|---|---|
| 5 | 55 | .01% NH$_4$VO$_3$ | 1.0 | 1.0 | 55 | con | 6.39 | 27 | 10 | 43 | .07 | .17 |
| 5 | 55 | .01% | 1.0 | 1.0 | 55 | counter | 4.52 | 26 | 16 | 31 | .06 | .20 |

TABLE III-continued

| Concn. (each by wt. %) per unit vol.) cyclohexanol and cyclohexanone | Concn. HNO3 (% w/w) | Catalyst (% w/v) | Flow Rate HNO3 (ml/min) | Flow Rate HC Feed (ml/min) | T | Concurrent or Countercurrent Flow | Adipic Acid (% w/v) | Glutaric/ Adipic (× 100) | Succinic/ Adipic (× 100) | Adipic Acid Yield (%) | Cyclohexanone Residual (% w/v) | Cyclohexanol Residual (% w/v) |
|---|---|---|---|---|---|---|---|---|---|---|---|---|
| 5 | 55 | NH4VO3 .01% | 3.8 | 3.8 | 55 | counter | 7.86 | 25 | 11 | 53 | .09 | .21 |
| 5 | 55 | NH4VO3 .05% | 1.0 | 1.0 | 55 | con | (6.29) (6.67) | 30 | 12 | 44 | .07 | .16 |
| 2.5 | 55 | NH4VO3 .01% | 2.0 | 3.8 | 55 | con | 3.66 | 25 | 9 | 25 | .09 | .06 |
| 2.5 | 55 | NH4VO3 .01% | 2.0 | 3.8 | 55 | con | 4.40 | 27 | 11 | 30 | .08 | .05 |
| 2.5 | 55 | NH4VO3 .37% Cu | 2.0 | 2.0 | 55 | con | 7.04 | 4 | 2 | 48 | .07 | .26 |
| 2.5 | 45 | .05% Cu | 1.0 | 2.0 | 55 | con | | | | | | |
| 2.5 | 45 | .05% Cu | 1.0 | 2.0 | 55 | con | 5.50 | 19 | 9 | 37 | .13 | .09 |
| 2.5 | 45 | .05% Cu | 1.0 | 2.0 | 55 | counter | 6.4, 7.5 | 22 | 9 | 43, 51 | .04 | .11 |

EXAMPLE 3

A solution of cyclohexanone and cyclohexanol in cyclohexane (2.5% w/v each) was introduced into the "outer tube" of the flow reactor at a flow rate of 2.0 ml/min. at a temperature of 55°. Simultaneously a solution freshly prepared from copper shot (0.05% w/v) dissolved in 45% (w/w) nitric acid was introduced into the "inner tube" (within the Nafion membrane) at a flow rate of 1.0 ml/min. After several volumes of reactants had passed through the reactor, the delivery syringes were marked for delivery volumes and the effluents were collected in graduated cylinders. This procedure was used for both concurrent and countercurrent flow of reactants. Small samples were removed for later analysis by gas chromatography. The bulk samples from the nitric acid phase were heated at 97° for 15 min. to complete the conversion of residual ketone and alcohol, then cooled to 5° to allow crystallization of adipic acid. Bulk samples from the cyclohexane phase were cooled for crystallization of adipic acid. The adipic acid was collected in tared filter crucibles and dried overnight (m.p. 153-4—uncorr.—"first crop"). The filtrates were separately reduced to dryness and the residue taken up in a small amount of water and filtered to provide a "second crop" of product.

Both the nitric acid phase and the cyclohexane phase were examined for residual ketone and alcohol in addition to adipic acid. The results are presented in Table IV.

TABLE IV

| Flow Method | ml HNO3 in | ml HNO3 out | hydrocarbon volume (ml) in | hydrocarbon volume (ml) out | HNO3 phase adipic acid (g) | Feed Phase adipic acid g | Adipic Acid total (g) HNO3 phase | Adipic Acid total (g) Feed | % yield as adipic acid |
|---|---|---|---|---|---|---|---|---|---|
| concurrent | 38 | 38 | 76 | 72 | 1st crop 1.5414 2nd crop 1.6305 | 1st crop 0.0652 2nd crop 0.2215 | 3.17 | 0.284 | 61 |
| countercurrent | 38 | 38 | 76 | 68 | 1st crop 1.4870 2nd crop 1.2189 | 0.1216 0.2876 | 2.71 | 0.41 | 56 |

Gas Chromatographic Analysis

| Flow Method | (cyclohexanone) (% w/v) | % Extraction | (Cyclohexanol) | % Extraction | Adipic Acid HNO3 phase (% w/v) | Yield | $\left(\frac{glutaric\ acid}{adipic\ acid}\times 100\right)$ | $\left(\frac{succinic\ acid}{adipic\ acid}\times 100\right)$ |
|---|---|---|---|---|---|---|---|---|
| Concurrent | 0.04, 0.03 | 98–99% | 0.10, 0.11 | 96 | 6.4–7.5% | 51% | 21–23 | 11 |
| Countercurrent | 0.13, 0.13 | 95% | 0.09, 0.15 | 94, 96 | 5.5–5.8% | 39% | 24–27 | 9 |

EXAMPLE 4

To further illustrate the scope of the instant invention, the oxidation of cyclododecane was conducted in the flow reactor previously described, using concurrent flow. The mixture employed was 5.0% (w/w) cyclododecanone (CDDone) in cyclododecane (CDD). The results are described in Table V. (DDA represents 1, 10 dodecanedioic acid.)

TABLE V

| T (°C.) | HNO3 (% w/w) | (Cu++) (% w/v) | Approx. Flow Rates ml/min | Residual Concn. CDDone (% w/v) | Concn. CDDone | Concn. (% w/v) DDA out HNO3 phase | Concn. DDA out % w/v CDD phase |
|---|---|---|---|---|---|---|---|
| 60 | 45 | .05% | 0.5–1.0 | 4.5 | 5.0 | 0.14 | |
| 70 | 45 | .05 | 11 | 4.4 | 5.0 | 0.14 | |
| 85 | 45 | .05 | 11 | 3.4, 4.0 | 5.0 | 0.25, 0.28 | |
| 97 | 55 | 0.2, 0.05% NH4VO3 | 0.5 | 0.9, 0.9 | 5.0 | 1.03, 1.51 | 0.25, 0.30 |
| 97.5 | 55 | 0.2, 0.05% NH4VO3 | 0.5-HNO3 1-CDD | 1.48, 1.51 | 5.0 | 1.48, 1.51 | 1.34, 1.95 |

TABLE V-continued

| T (°C.) | $HNO_3$ (% w/w) | ($Cu^{++}$) (% w/v) | Approx. Flow Rates ml/min | Residual Concn. CDDone (% w/v) | Concn. CDDone | Concn. (% w/v) DDA out $HNO_3$ phase | Concn. DDA out % w/v CDD phase |
|---|---|---|---|---|---|---|---|
| 97 | 55 | 0.2, 0.05% $NH_4VO_3$ | 0.5 | 0.0 | 0.11–0.14 | 0.94–1.15% | 0.24–0.30 |

EXAMPLE 5

The above experiments with nitric acid oxidation of the permeated cyclohexanone and cyclohexanol were repeated utilizing chromic acid as the oxidant in the permeate zone to convert said permeating compounds into adipic acid. The pressure of the extraction was held at approximately 10 psig in both the dialysis cell and the flow cell to keep the cyclohexane feed in the liquid state.

In the dialysis cell experiment, 1.0 wt. % per unit volume each of cyclohexanol and cyclohexanone dissolved in cyclohexane was placed in the feed zone. A chromic acid solution comprising 0.5 Mole $CrO_3$ dissolved in 1.0 Molar $H_2SO_4$ was placed in the permeate zone. The reaction temperature was held at 57° C. Table VI shows the concentration of adipic acid in the chromic acid phase as a function of time. It was noted that in comparison with similar reactions using nitric acid in the permeate zone, an increase in the rate constant was the same within a factor of 2. It was also noted that no adipic acid or chromium salts were observed in the feed zone of the permeation apparatus.

Use of chromic acid as an oxidant was investigated using the tubular flow reactor described above. The feed and the chromic acid were flowed concurrently on opposite sides of the Nafion membrane at approximately equivalent rates. As can be seen from Table VII, increased adipic acid production is favored by higher temperature, lower flow rate and increased acid concentration. It is noted also that very small concentrations of other dicarboxylic acids, i.e. less than 10 wt. % of the total (principally glutaric and succinic acid), were observed. Again, all the adipic acid was formed in the chromic acid phase. It is noted that chromic acid provides an advantage over nitric acid oxidation in that the reaction is somewhat more specific for adipic acid production.

The experiment with the tubular flow reactor was repeated. (See the last experiment in Table VII). The temperature of the contacting was 80° C. and flow rates of 0.4 milliliters per minute were maintained on both sides of the tubular membrane. 1.9 wt. % each of cyclohexanol and cyclohexanone in cyclohexane was used as the feed. The chromic acid oxidant comprised 0.97M $CrO_3$ in 2.1M $H_2SO_4$. When more than a reactor volume of reagents had passed through the reactor, the effluents from both sides of the membrane were collected. At this point, 26.2 milliliters of feed and 35.3 milliliters of oxidant had passed through the reactor. Both the oxidant and the feed phase were analyzed. The feed phase contained 0.86 wt. % per unit volume cyclohexanone and no cyclohexanol nor adipic acid. The chromic acid phase contained 3.7 wt. % per unit volume adipic acid and only trace amounts of succinic and glutaric acids, i.e. less than 0.3 wt. % per unit volume total. An aliquot from the aqueous chromic acid effluent was cooled to 5° C. and maintained at that temperature overnight. The adipic acid was removed by filtering, washed twice with small amounts of water and then dried in vacuum overnight. A product having a melting point of 153 to 155.5° C. was obtained. Based on conversion of ketone and alcohol, the yield of adipic acid is 114% as calculated by gas chromatography (described above) and 73% by isolation.

The use of chromic acid as an oxidant in a process for converting cyclohexanone and cyclohexanol into adipic acid has the following advantages over use of nitric acid. (1) The product has a higher degree of purity as well as an increased yield. (2) The safety and engineering problems associated with the use of nitrogen oxides in contact with cyclohexane are avoided. (3) Phase separation is excellent, i.e. no cyclohexanone was observed in the chromic acid effluent and very little water was observed in the cyclohexane effluent. Furthermore, no evidence of chromium salts was observed in the cyclohexane effluent.

TABLE VI

| Adipic Acid (wt. %/vol.) | Time (minutes) |
|---|---|
| 0.05 | 0 |
| .12 | 10 |
| .24 | 20 |
| .39 | 30 |
| .41 | 40 |
| .60 | 50 |
| .75 | 60 |
| .80 | 70 |
| .87 | 80 |
| .96 | 90 |
| .99 | 100 |
| 1.07 | 110 |
| 1.08 | 120 |
| 1.18 | 130 |
| 1.19 | 140 |
| 1.21 | 150 |

TABLE VII

| Experiment (°C.) T | (ml/min) Flow | (m) ($CrO_3$) | (m) ($H_2SO_4$) | (% w/v) Cyclohexanone Residual | (% w/v) Cyclohexanol Residual | (% w/v) (Adipic Acid) $CrO_3$ phase | % w/v (Adipic Acid) feed | Adipic Yield (based on 100% Conv.) | (based on feed conv.) |
|---|---|---|---|---|---|---|---|---|---|
| 70 | 0.5 | 0.5 | 1.0 | 1.8 | N | 1.8 | — | 32 | 62 |
| 70 | 1.0 | 0.5 | 1.0 | 2.3 | 0.1 | 1.4 | — | 25 | 69 |
| 70 | 0.5 | 0.5 | 1.0 | 2.9 | 0.1 | 1.33 | — | 23.5 | 114 |
| 70 | 0.25 | 0.5 | 1.0 | 1.9 | N | 1.97 | — | 35 | 71 |
| 70 | 1.0 | 0.5 | 1.0 | 2.1 | N | 1.29 | — | 23 | 51 |
| 70 | 1.0 | 0.5 | 2.0 | 1.8 | N | 2.50 | — | 44 | 86 |
| 76 | 1.0 | 0.5 | 2.0 | 1.7 | N | 3.60 | — | 64 | 115 |

TABLE VII-continued

| Experiment (°C.) T | (ml/min) Flow | (m) (CrO$_3$) | (m) (H$_2$SO$_4$) | (% w/v) Cyclohexanone Residual | (% w/v) Cyclohexanol Residual | (% w/v) (Adipic Acid) CrO$_3$ phase | % w/v (Adipic Acid) feed | Adipic Yield (based on 100% Conv.) | (based on feed conv.) |
|---|---|---|---|---|---|---|---|---|---|
| 76 | 0.5 | 0.5 | 2.0 | 0.43 | N | 4.52 | — | 80 | 91 |
| 76 | 0.5 | 0.5 | 2.0 | 0.93, 0.85 | N | 1.91 | — | 34 | 44 |
| 80 | 0.37 | 0.97 | 2.13 | 0.93 | N | 3.8 | 0 | 89 | 114 |

N = nil
— = not analyzed

EXAMPLE 6

In another experiment with the tubular flow reactor chromic acid was used to partially oxidize cyclohexanol from a 4% (w/v) solution in cyclohexane. The results are shown in Table VIII.

In the above experiment, the cyclohexanone reaction product was extracted back into the cyclohexane and the remainder was in the chromic acid phase. A second extraction by cyclohexane of the chromic acid phase would increase the product recovery. Better recovery would be obtainable with alcohol-ketone pairs which partition more in favor of the hydrocarbon phase (e.g. steroid alcohols).

page 189, (1963), Wiley & Sons.) In contrast to this cumbersome procedure, the present process can simply contact the alcohol such as a steroid alcohol in admixture with a hydrocarbon or oxygenated hydrocarbon solvent (e.g., ether) with the polymeric membrane having on the other side an aqueous chromic acid solution which oxidizes the diffusing alcohol to the ketone which can be extracted immediately in the reverse direction back into the hydrocarbon phase to minimize the cleavage of the ketone.

The combined membrane solvent extraction and conversion process of the invention in addition to the foregoing examples may be applied to the following systems which are further illustrative but not limiting. These

TABLE VIII

Oxidation of Cyclohexanol (4.0% (w/v) in Cyclohexane) to Cyclohexanone by Chromic Acid.

| T (°C.) | Flow (ml/min) | (m) (CrO$_3$) | (m) H$_2$SO$_4$ | (% w/v) Cyclohexanol Residual | (% w/v) (Adipic) CrO$_3$ Phase | (% w/v) (Adipic) Feed | (% w/v) (Cyclohexanone) Feed | % Yield of Cyclohexanone (Based on Converted Cyclohexanol) |
|---|---|---|---|---|---|---|---|---|
| 50 | 1.0 | 0.5 | 2M | 0.44 | 1.20 | 0.007 | 2.2 | 63 |
| 50 | 0.5 | 0.5 | 2 | 0.03 | 1.54 | 0.01 | 2.5 | 64 |
| 50 | 0.25 | 0.5 | 2 | N | 1.80 | 0.07 | 2.3 | 59 |
| 40.5 | 0.25 | 0.24 | 2.2 | 0.083 | 0.281 | 0.0029 | 1.38 | 36 |
| 40.5 | 0.5 | 0.24 | 2.2 | 0.72 | 0.293 | 0.0076 | 1.76 | 55 |
| 40.5 | 1.0 | 0.24 | 2.2 | 1.19 | 0.356 | 0.0044 | 1.03 | 28 |
| 40.5 | 0.25 | 1.0 | 2.2 | 0.48 | 0.20 | 0.0024 | 1.75 | 50 |
| 40.5 | 0.5 | 1.0 | 2.2 | 0.047 | 1.80 | 0.0104 | 2.12 | 55 |
| 40.5 | 1.0 | 1.0 | 2.2 | 0.45 | 1.15 | 0.0099 | 1.52 | 43 |
| 50 | 0.25 | 0.24 | 2.2 | 0.57 | 0.187 | 0.0035 | 2.16 | 63 |
| 50 | 0.5 | 0.24 | 2.2 | 0.74 | 0.257 | 0.0036 | 2.04 | 63 |

Further the combined membrane solvent extraction and conversion process of the present invention can be especially useful in converting alcohols to ketones as a replacement for the complex procedure used in the Jones oxidation reaction. Thus the Jones reaction is customarily carried out as follows: Starting with an admixture of a secondary alcohol in acetone with some water at low temperatures such as 5° C., chromic oxide in sulfuric acid is dropped in until the orange color of chromic acid persists, indicating the completion of formation of the ketone conversion product. In the latter stages of the addition the ketone product is present in increasing concentration and may react with the added chromic acid to give undesired acid cleavage products (acids or diacids). For workup, ether or other organic solvent is added to precipitate the chromium salts and extract the ketone by phase separation. Water is then used to extract the residual chromium salts from the ether phase. (More detailed descriptions of the Jones' reaction are given by A. S. Hussey and R. H. Baker, J. Organic Chemistry Vol. 25, page 1434 (1960) and by L. F. Fieser in "Organic Synthesis", Collective Vol. 4, systems are listed with five columns, A, B, C, D and E in Table IX. A is a solute or solutes present in minor amounts down to traces in the feed solvent; B is the feed solvent liquid initially containing solute A; C is the extracting solvent liquid into which the solute diffuses or permeates; D is the reactant such as oxidant, reducing agent, esterification agent or other conversion reactant; E is the nature of the reaction products. Any of the various polymeric membrane materials described hereinabove can be used provided that, as will be apparent to one skilled in the art, the membrane will allow diffusion of the solute and is non-reactive with the selected solute, solvents, reactant and reaction products under the operating conditions. In these systems the membrane solvent extraction proceeds and the permeating solute is converted to a new chemical substance such that the solute concentration is effectively reduced in the extracting solvent, whereby a high concentration gradient for the solute across the membrane is maintained for improved separation for the solute from the feed solvent.

TABLE IX

| System No. | A Solute | B Feed Solvent | C Extracting Solvent | D Reactant | E Reaction Products |
|---|---|---|---|---|---|
| 1. | Methanol | Ethyl ether | Water | $HNO_3$ | $CO_2$ |
| 2. | Acetone | Ethyl ether | Water | $HNO_3$ | Acetic acid, $CO_2$ |
| 3. | Ethylene | Hexane | Water | Performic acid | Epoxide or glycol esters |
| 4. | Cyclohexene | Hexane | Water | K permanganate | Diacid |
| 5. | Cyclohexene | Hexane | Water | Osmium tetraoxide-$KMnO_4$ | Glycol |
| 6. | Butanol | Cyclohexane | Cyclohexane | Lauroyl chloride | Butyl laurate |
| 7. | Hexanol | Cyclohexane | Cyclohexane | Phenyl isocyanate | N—phenyl hexyl urethane |
| 8. | Methyl stearate | Hexane | Water | NaOH | Sodium stearate and methanol |
| 9. | Hydroxy steroid | Toluene | Water | Chromic acid | Keto steroid |
| 10. | Hydroxy steroid | Methylene chloride | Methylene chloride | Dicyclohexyl carbodimide, benzoic acid | Benzoate of hydroxy steroid, decylcyclohexyl urea |
| 11. | Keto steroid | Ethyl ether | Ethyl ether | Li Al hydride | Hydroxy steroid |
| 12. | Methanol | Benzene | Water | $HNO_3$ | $CO_2$ |
| 13. | Keto steroid | Ethyl acetate and methanol | Ethyl acetate and methanol | $NaBH_4$ | Hydroxy steroid |
| 14. | Lauryl alcohol | Cyclohexane | Water | Chromic acid | Lauryl aldehyde |
| 15. | Cyclohexanol | Cyclohexane | Water | Chromic acid | Cyclohexanone |
| 16. | 2-butanol | t-butanol | Water | Chromic acid | 2-butanone |
| 17. | Glycerol | Water | Benzene | $KMnO_4$ crown ether complex | $CO_2$ |

I claim:

1. In a process for membrane solvent extraction wherein a solute permeates through a polymeric membrane from a feed solvent liquid phase containing said solute to an extracting solvent liquid without direct contact betweeen the liquid phases which are separated by said membrane, the improvement which comprises maintaining a high concentration gradient for said solute across said membrane with an extracting solvent which has no greater solubility for the solute than said feed solvent by converting said solute permeating through said membrane to a different chemical compound by reacting the permeated solute with a reactant which is reactive with said solute but which is essentially non-reactive with said membrane and said solvents, thereby improving the separation of said solute from said feed solvent liquid phase.

2. The process of claim 1 wherein said extracting solvent liquid phase has substantially less solubility for said solute than said feed solvent liquid phase.

3. The process of claim 1 wherein said solute and feed solvent are partially oxygenated hydrocarbon and hydrocarbon, respectively, said extracting solvent is an aqueous solvent and in said conversion said permeated partially oxygenated hydrocarbon is oxidized to a higher oxygenated state by an oxidant in said extracting solvent.

4. The process of claim 3 wherein said partially oxygenated hydrocarbons are selected from the group consisting of alcohols, ketones and mixtures thereof and said more highly oxygenated hydrocarbons are carboxylic acids and mixtures thereof.

5. The process of claim 3 wherein the product of said oxidation is more soluble in said aqueous solvent than said partially oxidized hydrocarbon in said aqueous solvent.

6. The process of claim 3 wherein said solute and feed solvent together form a liquid phase admixture obtained from liquid phase air oxidation of aliphatic hydrocarbon.

7. The process of claim 6 wherein said admixture consists essentially of cyclohexanone and cyclohexanol in cyclohexane.

8. The process of claim 7 wherein said extracting solvent is an aqueous solvent containing an oxidant selected from nitric acid and chromic acid.

9. The process of claim 7, wherein said oxidant is nitric acid.

10. The process of claim 7 wherein said extracting solvent is an aqueous solution of chromic acid.

* * * * *